United States Patent [19]

McMahon

[11] 4,064,175
[45] Dec. 20, 1977

[54] ORGANIC NITROGEN-CONTAINING INITIATORS FOR HYDROCARBON CONVERSION

[75] Inventor: Matthew A. McMahon, Wappingers Falls, N.Y.

[73] Assignee: Texaco Inc., New York, N.Y.

[21] Appl. No.: 729,557

[22] Filed: Oct. 4, 1976

[51] Int. Cl.$^2$ .................... C07C 27/12; C07C 29/00; C07C 45/02
[52] U.S. Cl. .................. 260/586 P; 260/466; 260/467; 260/514 J; 260/514 K; 260/515 R; 260/515 A; 260/521 B; 260/526 R; 260/526 S; 260/535 R; 260/535 H; 260/539 R; 260/539 A; 260/590 R; 260/591; 260/592; 260/597 R; 260/598; 260/600 R; 260/604 R; 260/617 H; 260/618 C; 260/631 R; 260/632 C; 260/644; 260/645; 260/646

[58] Field of Search .......... 260/586 P, 631 R, 617 H, 260/597 R, 597 T, 592, 618 C, 590 R, 632 C, 633, 599, 604 R

[56] References Cited

U.S. PATENT DOCUMENTS

| | | | |
|---|---|---|---|
| 2,565,087 | 8/1951 | Porter et al. | 260/631 R |
| 2,790,004 | 4/1957 | Dougherty | 260/586 P |
| 2,825,742 | 3/1958 | Schmelu et al. | 260/631 R |
| 2,851,496 | 9/1958 | Cates et al. | 260/586 P |
| 3,274,254 | 9/1966 | Seddon | 260/586 P |
| 3,870,760 | 3/1975 | Tanaka et al. | 260/617 H |

*Primary Examiner*—Norman Morgenstern
*Attorney, Agent, or Firm*—Thomas H. Whaley; Carl G. Ries; Carl G. Seutter

[57] ABSTRACT

Chemical reactions of hydrocarbons may be selectively initiated to produce increased yield of desired products by the use of initiators typified by alkyl nitrites such as n-butyl nitrite.

16 Claims, No Drawings

ORGANIC NITROGEN-CONTAINING INITIATORS FOR HYDROCARBON CONVERSION

FIELD OF THE INVENTION

This invention relates to hydrocarbon conversion. More particularly, it relates to the conversion of hydrocarbons in the presence of novel initiator systems.

BACKGROUND OF THE INVENTION

As is well known to those skilled in the art, hydrocarbons may be converted to a variety of products. Among the problems which have been encountered in such processes are (i) the problem of control of the reaction to yield preferred products; (ii) the problem of initiating the reaction to permit attainment of satisfactory yields of product by reaction at moderate conditions; and (iii) the problem of increasing the rate of reaction so as to minimize the size of the reactor required to produce desired amount of product.

In prior art processes wherein nitrogen compounds such as n-butyl nitrite have been reacted with hydrocarbons such as cyclohexane, the principal reaction products are found to be nitro-compounds. For example, U.S. Pat. No. 2,883,433 shows reaction, at elevated temperature and pressure in an oxygen-free environment, of cyclohexane and n-butyl nitrite to give 32% yield of the desired nitrocyclohexane "and oxidation products in 5.6% yield". Reaction is carried out at 140° – 300° C and pressure greater than 125 psig. When the reaction temperature was lowered from 145° C down to 125° C, "no nitration occurred". The reaction is characterized as occurring "without the formation of appreciable quantities of undesired oxidation products".

It is known — Chow et al., Canadian Journal of Chemistry, Vol. 48, 1970, pages 508–511 — that in the presence of light and oxygen, 1-octyl nitrite inter alia may be photolyzed to produce 1-octyl nitrate. Similar results are achieved for 1-pentyl nitrite, etc. Reactions of $NO_x$ or of nitrites are set forth also in Emanual et al, Liquid Phase Oxidation of Hydrocarbons, Plenum Press (1967) and in Walling, Free Radicals in Solution, J. Wiley (1957).

These references are characterized inter alia by the production of various nitrogen-containing compositions. They do not desire to produce oxygenated compounds (with minimum production of nitrogen-containing compounds); and they do not succeed in producing oxygen-containing compounds. See also U.S. Pat. No. 3,948,992 (of the instant inventor) for additional background.

OBJECTS OF THE INVENTION

It is an object of this invention to provide a process for preparing reaction products of hydrocarbons. Other objects will be apparent to those skilled in the art.

STATEMENT OF THE INVENTION

In accordance with certain of its aspects, the process of this invention for preparing an oxygen-containing oxidation product of an alkyl, alkaryl or cycloalkyl hydrocarbon may comprise:

oxidizing alkyl, alkaryl or cycloalkyl hydrocarbon at 75°–200° C in the presence of (i) an oxygen-containing gas and (ii) an oxidation initiator containing an initiating quantity of an alkyl, aralkyl or cycloalkyl nitrite, thereby forming reaction mixture including said oxygen-containing oxidation product and recovering said reaction mixture including said oxygen-containing oxidation product.

DESCRIPTION OF THE INVENTION

The hydrocarbons which may be treated by the process of this invention may be characterized by the formula RH. In the above compound, R may be hydrocarbon radical selected from the group consisting of alkyl, alkaryl and cycloalkyl including such radicals when inertly substituted. When R is alkyl it may typically be methyl, ethyl, n-propyl, iso-propyl, n-butyl, i-butyl, sec-butyl, amyl, octyl, decyl, octadecyl, etc. When R is alkaryl it may typically be tolyl, ethylphenyl, etc. When R is cycloalkyl it may typically be cyclohexyl, cycloheptyl, cyclooctyl, 2-methylcycloheptyl, 3-butylcyclohexyl, 3-methylcyclohexyl, etc. R may be inertly substituted, i.e. it may bear a nonreactive substituent such as aryl, halogen, nitro, carboxyl, etc. Typically, inertly-substituted R groups may include 3-chloropropyl, p-chloromethylphenyl, etc. The preferred R groups may be lower alkyl, i.e. $C_1$–$C_{10}$ alkyl, groups including, e.g, methyl, ethyl, n-propyl, i-propyl, butyls, amyls, hexyls, octyls, decyls, etc. R may be preferably cyclohexyl.

Typical hydrocarbons which may be treated by the process of this invention may be butane, pentane, hexane, octanes, etc. The process of this invention is particularly characterized by its ability to oxidize naphthenes, including cyclohexane, methyl cyclohexane, cyclopentane, methyl cyclopentane, etc., and alkyl-bearing aromatics such as toluene, xylene, n-propyl benzene, etc. The preferred hydrocarbon charge may be a cyclohexane and preferably cyclohexane per se.

It is a feature of the process of this invention that reaction of the charge hydrocarbon RH is carried out in the presence of an oxidation initiator containing an initiating quantity of an alkyl, aralkyl or cycloalkyl nitrite. The alkyl nitrite, aralkyl nitrite, or cycloalkyl nitrite may be characterized by the formula R'ONO wherein R' may be selected from the group consisting of alkyl, aralkyl, and cycloalkyl. When R' is alkyl or cycloalkyl, it may be selected from the same group as when R is alkyl or cycloalkyl. When R; is aralkyl, it may be benzyl, betaphenylethyl, etc. R' may be the same as R or it may be different. In one preferred embodiment the hydrocarbon may be cyclohexane and the oxidation initiator may be n-butyl nitrite or cyclohexyl nitrite.

The charge hydrocarbon may be a mixture of hydrocarbons designated as a petroleum naphtha, a $C_{10}$–$C_{14}$ paraffin cut, a petroleum wax, etc. — in which case, of course, the product may also be a mixture.

The nitrites, such as butyl nitrite, may be commercially available or, alternatively, they may be prepared from the corresponding alcohol as, e.g., by the procedure for preparing butyl nitrite at Organic Synthesis, Collected Volume 2, page 108.

Illustrative nitrites which may be employed may include the following:
n-propyl nitrite
n-butyl nitrite
t-butyl nitrite
i-butyl nitrite
2-ethylhexyl nitrite
cyclohexyl nitrite
benzyl nitrite amyl nitrite The preferred nitrite may be a lower alkyl nitrite, typically a $C_2$ to $C_5$ alkyl nitrite. Preferred may be n-propyl nitrite or n-butyl nitrite.

The initiating quantity (in moles) of oxidation initiator per 100 moles of hydrocarbon charge may be 0.05-20, preferably 0.5-10, say 5.

In practice of the process of this invention, there may be admitted to the reaction zone an oxygen-containing gas in amount to provide 1-25 moles, preferably 5-10 moles, say 10 moles, of oxygen per 100 moles of charge hydrocarbon, e.g. cyclohexane. Typically, this may be admitted as air, oxygen-enriched air or, more preferably, oxygen of 90-100% purity.

Preferably, the oxidation of the hydrocarbon may be carried out at 75°-200° C, typically 125°-150° C, say 125° C, and 0-300 psig, typically 0-75 psig, say 75 psig, for 1-120 minutes, typically 30-100 minutes, say 60 minutes. It is a particular characteristic of the process of this invention that it gives desired yields of product oxygen-containing compounds at low temperatures. For example, at 125° C it is possible to attain desired oxygen-containing products in typical yield of 70.0 mole percent (based upon cyclohexane converted); and the desired ratio of oxygen-containing products to nitrogen-containing products may be 2.34:1. In contrast, prior art reactions, typified by those of U.S. Pat. No. 2,883,433 (Example I), give a ratio of only 0.175:1 at a higher temperature of 145° C.

It is also a characteristic of the process of this invention that it gives desired yields of product oxygen-containing compounds at low pressure. The above illustrative process of this invention, operating at, e.g. 75 psig, provides desired yield. In contrast, the illustrative prior art requires operation at "pressure of at least 125 psig".

In carrying out the process of this invention, there may be admitted to the reaction operation 100 moles of charge hydrocarbon, typically cyclohexane; and oxygen-containing gas in amount to provide 1-25, preferably 5-10, say 10, moles of oxygen; and 0.05-20, preferably 0.5-10, say 5, moles of an alkyl nitrite, an aralkyl nitrite or a cycloalkyl nitrite—preferably normal butyl nitrite.

Reaction occurs in liquid phase in the absence of catalyst. Typical reaction time in the laboratory may be 0.25-5, preferably 0.5-2, say about one hour. In commercial practice it may be desirable to carry out continuous operation at a WHSV of 0.1-1, preferably 0.5-1, say about one.

During the course of the reaction it may be found that the charge hydrocarbon is converted to oxygenated compounds with only lesser amounts of nitro compounds. In one typical case of 100 moles of cyclohexane reacting with 10 moles of oxygen in the presence of 5 moles of n-butyl nitrite, for example, at 125° C and ca 75 psig, the product yields (based upon cyclohexane converted) may illustratively be 57.1 mole percent cyclohexanol, 12.9 mole percent cyclohexanone, 27.2 mole percent of cyclohexyl nitrate, and 2.6 mole percent nitrocyclohexane. The mole ratio of oxygenated products to nitrogen-containing products is thus (12.9+57.1)/(27.2+2.6) or 2.35.

The ratio of alcohol to ketone (e.g. cyclohexanol: cyclohexanone) in the product may be increased by increasing the concentration of nitrite (e.g. BUONO - n-butyl nitrite). For example, at a constant pressure of oxygen (1.0 m moles of oxygen per 24 moles of cyclohexane, corresponding to an oxygen partial pressure of 1670 mm Hg.) at 125° C, the following is noted:

| Concentration of BUONO as Wt. % of Cyclohexane | Ratio of Cyclohexanol to Cyclohexanone in Product |
| --- | --- |
| 1 | 2.2 |
| 5 | 5.2 |
| 10 | 8 |

Similarly, it is possible to control the ratio of alcohol to ketone in the product. This ratio may be increased by decreasing the ratio of oxygen to nitrite. In a typical example, at varying oxygen pressure and at temperature of 125° C, as the ratio, in moles of oxygen per mole of n-butyl nitrite, is as noted in Column 1 infra, the product stream, after one hour, is found to have a mole ratio of cyclohexanol to cyclohexanone as noted in Column 2:

| 1 Oxygen (moles) | 2 Cyclohexanol (moles) |
| --- | --- |
| BUONO (moles) | Cyclohexanone (moles) |
| 5.0 | 2.2 |
| 4.0 | 2.5 |
| 3.0 | 3 |
| 2.0 | 3.7 |
| 1.0 | 5.5 |
| 0.5 | 8 |

It is thus possible to control the reaction toward increased selectivity to, e.g. cyclohexanol by using lesser quantities of oxygen (based on charge hydrocarbon) and by decreasing the ratio of oxygen to nitrite. Increased selectivity toward ketones is attained conversely.

As the concentration of butyl nitrite (on the basis of weight percent of charge, e.g. cyclohexane) increases, it is found that the concentration of nitrogen-containing products increases in the range of 1-10 wt. % n-butyl nitrite. The concentration of desired alcohol increases to a maximum (of about 0.17 moles per liter at 125° C and one hour reaction time) at about 6-7% n-butyl nitrite. The concentration of, e.g. cyclohexanone drops from a maximum at ca 1 wt. % n-butyl nitrite. Thus, maximum production of cyclohexanone may be attained at ca 1-2 wt. % n-butyl nitrite (based upon cyclohexane charged); and maximum cyclohexanol may be attained at ca 5-7 wt. % n-butyl nitrite.

Product mixtures may be recovered and worked up as by flashing to separate volatiles followed preferably by distillation of the remaining products.

DESCRIPTION OF PREFERRED EMBODIMENT

Practice of the process of this invention may be apparent to those skilled in the art from the following wherein, as elsewhere in this description, all parts are parts by weight unless otherwise stated.

Each of the examples was carried out in a standard laboratory glassware set-up which included a reaction vessel or flask which could be evacuated, subjected to pressure, cooled, and heated. These runs were carried out in the same apparatus used in and disclosed in applicant's U.S. Pat. No. 3,948,992.

In each example, the charge hydrocarbon, typically cyclohexane, was admitted. The stated quantity of nitrite (e.g. butyl nitrite) or other material was then added; and then oxygen was admitted in desired amount to a stated amount or pressure.

The system was then closed and maintained at reaction temperature and pressure. At the end of the reaction time, the system was cooled to room temperature; the liquid contents were analyzed by gas chromatography, or infra-red spectrophotometry.

In order to show the effect of variables such as time, temperature, concentration, etc., and the superiority over initiators falling outside the scope of the invention, many of the examples utilize cyclohexane as charge and n-butyl nitrite as initiator.

All examples, except where otherwise specifically noted, were carried with cyclohexane charge, oxygen and butyl nitrite (BUONO) as the initiator. The products, reported as weight percent of the charge cyclohexane converted, are shown as:

K — Cyclohexanone
A — Cyclohexanol
C — Cyclohexyl nitrate
N — Nitrocyclohexane

Certain of the examples indicated with an asterisk (*) are control examples; the others are experimental examples.

Abbreviations used in the tables include:
BUONO — normal butyl nitrite
DTBP — di-tertiary butyl peroxide
BHP — tertiary butyl hydroperoxide
PrONO — normal propyl nitrite All values in most of the tables are given as weight percent of the charge hydrocarbon converted, i.e. an entry of 0.5 means that of the charge hydrocarbon which was converted to other products, there is present 0.5% by weight of the specific noted product. The table reporting Examples XXX-XXXVII sets forth values in Relative Area % as determined by Gas Chromatographic Analysis.

EXAMPLES I–III

In this series of examples the charge included cyclohexane and oxygen. Example I included BUONO as the sole initiator. Example II included as the sole initiator a control: the same amount of di-t-butyl peroxide (DTBP) Example III included no additive — i.e., only cyclohexane and oxygen. The column headed "Total" shows the total oxidation products as wt. % of the converted charge.

TABLE

| Example | Initiator | K | A | C | Total |
|---------|-----------|------|------|------|-------|
| I | BUONO | 0.64 | 1.00 | 0.09 | 1.73 |
| II* | DTBP | 0.26 | 0.23 | 0.00 | 0.49 |
| III* | None | 0.055 | 0.031 | 0.00 | 0.086 |

Note: Initiator is present in amount of 0.01 moles per liter of cyclohexane. Reaction at 150° C and ca. 128 psig for 15 minutes in presence of 0.77 m moles of oxygen per ml. of cyclohexane. Ca 2 grams of cyclohexane charged (2.6 ml).

From Examples I–III it may be noted that use as an initiator of n-butyl nitrite (BUONO) permits attainment of desired oxygenated products (cyclohexanone and cyclohexanol) in amount which is almost four times greater than is obtained using the control initiator di-t-butyl peroxide in Example II* and which is about twenty times greater than is obtained using no initiator in Example III*.

EXAMPLES IV–VII

In this series of examples a comparison is made of the differences attained using (i) n-butyl nitrite and n-propyl nitrite and (ii) different amounts of oxygen.

In this series of runs, 2 grams of a solution of the designated nitrite in cyclohexane, and oxygen, were admitted to the reaction vessel and heated for 1 hour at 125° C. In Examples IV and VI, the initiator was one millimole of BUONO. In Examples V and VII, the initiator was one millimole of PrONO. In examples IV–V, oxygen was present in amount of 0.5 millimoles, and in Examples VI–VII, oxygen was present in amount of 1.5 millimoles.

TABLE

| Example | Nitrite | K | A | C | N |
|---------|---------|------|------|------|------|
| IV | BUONO | 6.5 | 48.9 | 38.1 | 6.5 |
| V | PrONO | 8.7 | 53.4 | 31.9 | 6.1 |
| VI | BUONO | 10.1 | 43.8 | 39.8 | 6.3 |
| VII | PrONO | 10.7 | 43.8 | 38.5 | 7.0 |

From the above table which shows the relative weight percent of the various products, it is apparent that the use of either normal butyl nitrite or normal propyl nitrite permits attainment of satisfactory results. It will be observed that the ratio of desired oxygenated products to nitrogen-containing products is 1.17–63; and the ratio of preferred alcohol to less preferred ketones is 4.1–6.12. It will also be noted that, at the lower oxygen content of Examples IV–V, the use of propyl nitrite gives ca 32% increase in the ratio of oxygenated products to nitrogen-containing product — although with a drop of about 20% in the ratio of alcohol to ketone. At the higher oxygen content, the results achieved with the propyl nitrite and the butyl nitrite are comparable.

EXAMPLE VIII

In this example the procedure of Examples IV–VII was duplicated, except that the initiator was present in amount of 0.01 moles of normal butyl nitrite per mole of charge cyclohexane. Reaction was carried out for 0.25 hours at 150° C in the presence of 2 millimoles of oxygen and about 2 grams of cyclohexane. Product composition is set forth in the table following Example XII, from which it may be seen that operation at 150° C is satisfactory.

EXAMPLES IX–XII

In this series of comparative examples the procedure of Examples IV–VII was duplicated, except as noted. Each reaction was carried out using about 2.0 grams of cyclohexane. Reaction was at 125° C for one hour. In experimental Example IX, the initiator is BUONO in amount of 0.146 moles per liter of cyclohexane. In control Examples I*–XI*, the initiator is BHP is amount of 0.146 moles per liter of cyclohexane. In Examples IX and XI*, the oxygen is present in amount of one millimole of oxygen, in Example X*, oxygen is present in amount of 0.8 millimoles; and in Example XII*, oxygen is present in amount of 1.5 millimoles.

TABLE

| Example | Initiator | K | A | C | | Total |
|---------|-----------|------|------|------|-----|-------|
| VIII | BUONO | 0.64 | 1.00 | 0.09 | — | 1.73 |
| IX | BUONO | 0.45 | 1.73 | 1.3 | 0.2 | 3.68 |
| X* | BHP | 0.18 | 0.29 | 0.0 | 0.0 | 0.47 |
| XI* | BHP | 0.28 | 0.41 | 0.0 | 0.0 | 0.69 |

TABLE-continued

| Example | Initiator | K | A | C | | Total |
|---|---|---|---|---|---|---|
| XII* | NONE | 0 | 0 | 0 | 0 | 0.00 |

From the above table it is apparent that use of butyl nitrite permits attainment of results which are superior to those attained using, e.g., t-butyl hydroperoxide or no initiator. For example, comparison of Examples IX and XI* reveals that it is possible to obtain about five times as much product using the process of the instant application than by use of initiators falling outside of the process of this application. Furthermore, the ratio of oxygenated products to nitrogen-containing products is maintained at a high level as is the ratio of desired alcohol to less desired ketone.

EXAMPLES XIII-XXIX

In this series of experimental runs the temperature of reaction was 125° C, except for Examples XXI-XXIII wherein it was 150° C. Reaction time was one hour in Examples XIII-XX; 0.5 hours in Examples XXI-XXIV and XXVIII; 1.5 hours in Examples XXV and XXIX; and 2.0 hours in Example XXVI. Concentration of BUONO was 5 wt. % in Examples XIII-XV, XXI-XXIII and XXVII-XXIX; 10 wt. % in Examples XVI-XVIII and XXIV-XXVI; and 1 wt. % in Examples XIX-XX.

The weight percent products and the cyclohexane conversion in weight percent are as follows:

TABLE

| Example | K | A | C | N | Cyclohexane Conversion |
|---|---|---|---|---|---|
| XIII | 0.19 | 1.46 | 1.14 | 0.20 | 2.99 |
| XIV | 0.36 | 2.18 | 1.85 | 0.35 | 4.74 |
| XV | 0.50 | 2.46 | 2.25 | 0.37 | 5.58 |
| XVI | 0.11 | 1.14 | 1.22 | 0.58 | 3.05 |
| XVII | 0.33 | 2.10 | 2.79 | 0.68 | 5.90 |
| XVIII | 0.40 | 2.23 | 3.53 | 0.65 | 6.81 |
| XIX | 0.34 | 1.31 | 0.77 | 0.17 | 2.59 |
| XX | 0.65 | 1.47 | 0.82 | 0.07 | 3.01 |
| XXI | 0.14 | 1.33 | 0.86 | 0.70 | 3.03 |
| XXII | 0.34 | 2.31 | 1.58 | 0.74 | 4.97 |
| XXIII | 0.50 | 2.46 | 1.93 | 0.70 | 5.59 |
| XXIV | 0.13 | 1.04 | 0.97 | 0.31 | 2.45 |
| XXV | 0.13 | 1.09 | 1.03 | 0.60 | 2.85 |
| XXVI | 0.11 | 1.06 | 0.99 | 0.52 | 2.68 |
| XXVII | 0.32 | 1.44 | 0.95 | — | 2.71 |
| XXVIII | 0.42 | 1.88 | 1.30 | 0.11 | 3.71 |
| XXIX | 0.35 | 1.95 | 1.50 | 0.34 | 4.14 |

EXAMPLES XXX-XXXVII

In this series of comparative examples the preferred BUONO initiators were used to oxidize toluene (Examples, XXX, XXXII, XXXIV, XXXVI and XXXVII) and cyclohexane (Examples XXXI, XXXIII and XXXV). In all cases the reaction time was 0.5 hours, except for Examples XXXVI-XXXVII wherein it was 3.0 hours. In all cases the amount of oxygen present was 0.5 millimoles, except in Example XXXVI wherein it was 1.0 millimole.

Temperature of reaction was:

| Example | Temperature |
|---|---|
| XXX-XXXI | 150° C |
| XXXII-XXXIII | 125° C |
| XXXIV-XXXV | 100° C |
| XXXVI-XXXVII | 75° C |

In each example the charge included about 2.0 grams of a 0.4 molar solution of n-butyl nitrite in either toluene or cyclohexane. The results are tabulated as before. It will be apparent that the designations K, A, C, N at the head of each column are as before for cyclohexane, but for those Examples XXX, XXXII, XXXIV and XXXVI-XXXVII using charge toluene they represent, respectively, benzaldehyde, benzyl alcohol, benzyl nitrate and nitromethyl benzene. Entries is this table are Relative area % as determined by Gas Chromatographic Analyses.

TABLE

| Example | K | A | C | N |
|---|---|---|---|---|
| XXX | 18.1 | 38.0 | 20.3 | 23.4 |
| XXXI | 4.4 | 49.6 | 22.9 | 22.9 |
| XXXII | 15.0 | 37.0 | 32.5 | 15.5 |
| XXXIII | 7.6 | 56 | 26.3 | 10.2 |
| XXXIV | 10.8 | 36.0 | 37.2 | 16 |
| XXXV | 16.7 | 50.0 | 33.0 | 0.0 |
| XXXVI | 18 | 20 | 58 | 4.5 |
| XXXVII | 27 | 27 | 37 | 8.3 |

From the above table the following will be apparent.
i. results attained with toluene are generally comparable to those attained with cyclohexane,
ii. the product generally contains more aldehyde than alcohol when toluene is the charge; and
iii. most satisfactory operation appears to be at 150° C—in terms of highest attainment of oxygenated products and lowest of nitrogen-containing products.

Results comparable to the above, e.g. Example I, may be attained when the initiator and hydrocarbon are:

| Example | Hydrocarbon | Initiator |
|---|---|---|
| XXXVIII | toluene | cyclohexyl nitrite |
| XXXIX | cyclohexane | cyclohexyl nitrite |
| XL | iso-octane | n-amyl nitrite |
| XLI | n-hexane | isoamyl nitrite |
| XLII | xylene | benzyl nitrite |
| XLIII | methylcyclopentane | iso-butyl nitrite |
| XLIV | xylene | 2-ethylhexyl nitrite |
| XLV | n-dodecane | cyclohexyl nitrite |
| XLVI | n-tetradecane | butyl nitrite |

Although this invention has been illustrated by reference to specific embodiments, it will be apparent to those skilled in the art that various changes and modifications may be made which clearly fall within the scope of this invention.

I claim:
1. The process for preparing an oxygen-containing oxidation product containing at least one composition selected from the group consisting of alcohols, ketones and aldehydes, from a charge alkyl, alkaryl or cycloalkyl hydrocarbon which comprises:
   oxidizing alkyl, alkaryl or cycloalkyl hydrocarbon at 75°-200° C in the presence of (i) an oxygen-containing gas and (ii) an oxidation initiator containing an initiating quantity of an alkyl, aralkyl or cycloalkyl nitrite, thereby forming reaction mixture including said oxygen-containing oxidation product; and
   recovering said reaction mixture including said oxygen-containing oxidation product.
2. The process for preparing an oxygen-containing oxidation product as claimed in claim 1 wherein said hydrocarbon is a naphthene.
3. The process for preparing an oxygen-containing oxidation product as claimed in claim 1 wherein said hydrocarbon is cyclohexane.

4. The process for preparing an oxygen-containing oxidation product as claimed in claim 1 wherein said hydrocarbon is an alkaryl hydrocarbon.

5. The process for preparing an oxygen-containing oxidation product as claimed in claim 1 wherein said hydrocarbon is toluene.

6. The process for preparing an oxygen-containing oxidation product as claimed in claim 1 wherein said oxidation initiator is a lower alkyl nitrite.

7. The process for preparing an oxygen-containing oxidation product as claimed in claim 1 wherein said oxidation initiator is butyl nitrite.

8. The process for preparing an oxygen-containing oxidation product as claimed in claim 1 wherein said oxidation initiator is propyl nitrite.

9. The process for preparing an oxygen-containing oxidation product as claimed in claim 1 wherein said oxidation initiator is cyclohexyl nitrite.

10. The process for preparing an oxygen-containing oxidation product as claimed in claim 1 wherein said initiating quantity is 0.05–20 moles of oxidation initiator per 100 moles of charge hydrocarbon.

11. The process for preparing an oxygen-containing oxidation product as claimed in claim 1 wherein said initiating quantity is 0.5–10 moles of oxidation initiator per 100 moles of charge hydrocarbon.

12. The process for preparing an oxygen-containing oxidation product as claimed in claim 1 wherein said process is carried out at 125°–150° C.

13. The process for preparing an oxygen-containing oxidation product as claimed in claim 1 wherein said process is carried out at 0–300 psig.

14. The process for preparing an oxygen-containing oxidation product containing at least one composition selected from the group consisting of alcohols, ketones and aldehydes, from a charge naphthene hydrocarbon which comprises:

oxidizing said charge naphthene hydrocarbon at 75°–200° C and 0–300 psig in the presence of an oxygen-containing gas and 0.5–10 moles, per 100 moles of charge naphthene hydrocarbon, of a lower alkyl nitrite, thereby forming reaction mixture including said oxygen-containing oxidation product; and recovering said reaction mixture including said oxygen-containing oxidation product.

15. The process for oxidizing cyclohexane to form an oxidation product containing cyclohexanol and cyclohexanone which comprises oxidizing said cyclohexane in the presence of oxygen-containing gas and, as oxidation initiator, a lower alkyl nitrite, thereby forming said oxidation product; and recovering said oxidation product.

16. The process as claimed in claim 15 wherein said oxidation initiator is butyl nitrite.

* * * * *